United States Patent [19]

Lawrie

[11] 4,174,255

[45] Nov. 13, 1979

[54] APPARATUS FOR LOCATING DEFECTIVE NUCLEAR FUEL ELEMENTS

[75] Inventor: William E. Lawrie, Lynchburg, Va.

[73] Assignee: The Babcock & Wilcox Company, New York, N.Y.

[21] Appl. No.: 794,508

[22] Filed: May 6, 1977

[51] Int. Cl.² .............................................. G21C 17/00
[52] U.S. Cl. .................... 176/19 LD; 73/659
[58] Field of Search ..................... 176/19 R, 19 LD; 73/659

[56] References Cited

U.S. PATENT DOCUMENTS

| 3,945,245 | 3/1976 | Stehle et al. | 176/19 R |
| 4,008,455 | 2/1977 | Pedersen | 176/19 R |
| 4,009,616 | 3/1977 | Wonn | 176/19 LD |
| 4,036,686 | 7/1977 | Weilbacher et al. | 176/19 R |
| 4,048,009 | 7/1977 | Weilbacher | 176/19 R |

FOREIGN PATENT DOCUMENTS

| 2528422 | 12/1976 | Fed. Rep. of Germany | 176/19 LD |
| 7703590 | 2/1977 | France | 176/19 LD |
| 47-16597 | 12/1972 | Japan | 176/19 LD |

Primary Examiner—Samuel W. Engle
Assistant Examiner—S. A. Cangialosi
Attorney, Agent, or Firm—Joseph M. Maguire; Angelo Notaro

[57] ABSTRACT

An ultrasonic search unit for locating defective fuel elements within a fuel assembly used in a water cooled nuclear reactor is presented. The unit is capable of freely traversing the restricted spaces between the fuel elements.

14 Claims, 7 Drawing Figures

APPARATUS FOR LOCATING DEFECTIVE NUCLEAR FUEL ELEMENTS

BACKGROUND OF THE INVENTION

1. Field of the Invention

This invention relates to nuclear reactors and, in particular, to an apparatus for locating defective fuel elements.

2. Description of the Prior Art

In water cooled heterogeneous reactors, a multiplicity of elongated fuel elements and control element guide tubes are arranged, as a closely spaced array, in a unified structure called a fuel assembly. The reactor core is generally comprised of a lattice of vertically disposed fuel assemblies.

Each of the elongated fuel elements, which are alternatively characterized as fuel rods, tubes or pins, contain nuclear fuel encapsulated by a thin cladding, plugged at its ends, that prevents erosion of the fuel and the release of fission products into the reactor coolant. Aluminum or its alloys, the stainless steels and zirconium are typical clad materials.

Plenum chambers and clearances are provided within the fuel elements to accommodate fission product gas released from the fuel, differential thermal expansion between the cladding and the fuel, and fuel density changes during burnup. The plenums are generally located at the ends of the fuel element and contain plenum springs which maintain the nuclear fuel in a fixed relationship. In some cases, the fuel elements are initially pressurized with a gas, typically helium, to minimize clad creep during prolonged periods of operation at high reactor coolant system pressures.

The fuel element cladding is designed to withstand the effects of the reactor operating environment including those due to coolant hydraulics, reactor temperature and pressure, fission gas pressure, fuel expansion, and irradiation growth. Some cladding defects, which permit the escape of radioactive fission products into the fluid coolant or moderator, however, may be expected to occur during the operating life of the reactor. Although purification systems are designed to remove the maximum amount of radioactivity expected to occur due to cladding defects, it may be desirable or necessary to detect and replace defective or "failed" fuel elements. Hence, it is important to have reliable means for locating defective fuel elements.

On one hand, locating a defective fuel element within a fuel assembly is extremely difficult since an assembly is radioactive and may contain hundreds of closely spaced fuel elements and guide tubes. On the other hand, disassembly and reassembly of irradiated fuel assemblies is time consuming and may, in itself, result in fuel element damage.

In reactors utilizing liquid coolants, a number of devices and techniques have been proposed for locating individual defective elements within the fuel assembly based upon detection and analysis of vibration, temperature differentials or ultrasonic phenomena.

These prior art detection devices and techniques have depended, in general, upon at least partial disassembly of a fuel assembly. Moreover, great dependence has been placed, in the prior art, on the dynamics of thermodynamic changes of state of the fluid which has leaked into the defective fuel element, typically boiling or condensation or both.

In order to facilitate the location of failed fuel elements within a fuel assembly, the development of a reliable method and apparatus which neither requires disassembly of a fuel assembly nor is dependent upon boiling or condensation of fluid within the fuel elements has been desired.

SUMMARY OF THE INVENTION

According to the present invention, in a fuel assembly of the type described above, a method and apparatus are provided for detecting defective fuel elements.

An ultrasonic search unit, made in accordance with the invention, is inserted into the spacing between components of the fuel assembly. The smallest spacing between fuel assembly components into which the transducer assembly must be inserted is on the order of two millimeters. In this respect, the search unit is comprised of a transducer element supported by a carrier which is capable of traversing the restrictive spacing. The transducer is aligned with the lower plenum of the fuel element to be tested.

It is known that ultrasound in the megahertz frequency range on the order of 5 to 15 megahertz is readily propagated through water. In contrast, at frequencies in this megahertz range, ultrasound attenuation is high in air or other gases. An ultrasonic pulse, at a frequency of a few megahertz, is transversely introduced into the wall of the fuel element. If the fuel element is not defective, then only gas will be in the lower plenum. The high reflection coefficient at the integral metal-gas interface will prevent significant propagation of the pulse past the inner surface of the cladding. If, in contrast, the fuel element has failed so that the lower plenum contains water, the reflection coefficient of the metal-liquid interface at the inner surface of the cladding will be reduced below that produced by a metal-gas interface. Thus, significant portions of the pulse will propagate through the water to the opposite wall, be reflected, and return to the transducer. Detection of the reflection from the opposite wall indicates that water has seeped into the fuel element.

The various features of novelty which characterize the invention are pointed out with particularity in the claims annexed to and forming a part of this specification. For a better understanding of the invention, its operating advantages and specific objects attained by its use, reference should be had to the accompanying drawing and descriptive matter in which there is illustrated and described a preferred embodiment of the invention.

BRIEF DESCRIPTION OF THE DRAWINGS

In the accompanying drawings, forming a part of this specification, and in which reference numerals shown in the drawings designate like or corresponding parts throughout the same.

DESCRIPTION OF THE PREFERRED EMBODIMENTS

Figure 1:
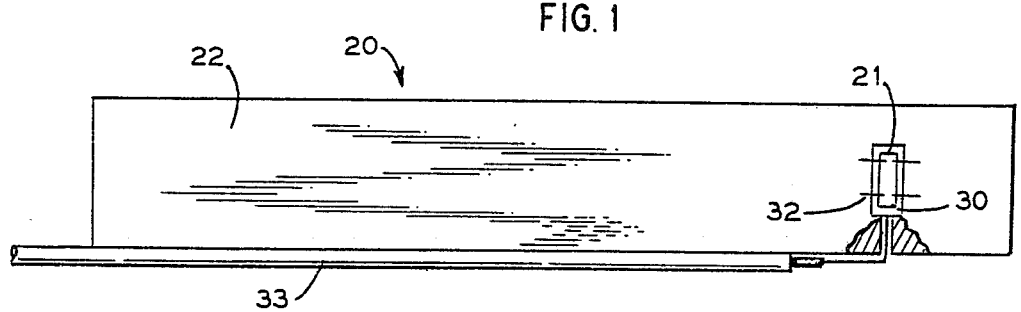
FIG. 1 is a front view of an apparatus made in accordance with the invention.
Figure 2:
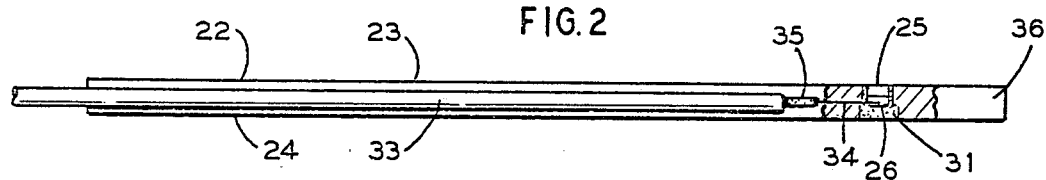
FIG. 2 is a bottom view, partly broken away, of the apparatus shown in FIG. 1.

FIG. 1 illustrates an ultrasonic search unit 20. The search unit 20 includes an ultrasonic transducer element 21 and a strip carrier 22 that, as is best shown in FIG. 2, has mutually opposing faces 23, 24, and an aperture in which the transducer element 21 is suitably mounted.

The transducer element 21, which is a polarized ferroelectric ceramic having an electrode deposited or fired on two of its surfaces, is aligned within the aperture so that one surface 25 is flush with face 23 of the strip carrier 22. The opposing surface of the transducer element is recessed within the aperture and faced by a sonic damping material 26. A decoupling isolating material 30 is placed between the perimeter of the aperture and the respective opposing surfaces of the element 21. The element 21 is secured within the aperture by an electrically non-conducting cement 31. The surface 25 of the transducer element 21 which is flush with face 23 of the strip carrier is grounded to the carrier. Grounding is accomplished by spot welding several conductors 32, or by other suitable means.

The decoupling material 30 is disposed between the transducer element and carrier in order to minimize ultrasonic coupling therebetween.

A coaxial cable 33, having an inner conductor 34 and an outer conductor 35, is attached to an edge 36 of the strip carrier. The inner conductor 34 is attached to the transducer element 21. The outer conductor 35 is attached to the strip carrier 22.

The search unit 20 must be capable of freely traversing the limited clearances between the fuel elements or between a fuel element and a control element guide tube of a fuel assembly which may be spaced to within two millimeters of each other. Hence, the search unit 20, as well as its individual components, must be selected to satisfy specific dimensional requirements without compromising the ultrasonic characteristics needed to apply the principles of the detection technique.

A specific example of a search unit constructed in accordance with the principles of the invention includes a transducer element fabricated from lead zirconate titanate, measuring approximately 2.5 millimeters wide, 12.5 millimeters long and 0.3 millimeters thick, mounted in an aluminum carrier. The transducer element is isolated from the perimeter of the aperture by a layer of cork. The front and back surfaces of the transducer element are coated with fired silver electrodes, and the surface that is flush with one face of the carrier is grounded to the adjacent aluminum at several points through small copper wires tack welded to both the aluminum and the silver electrode. A layer of the conducting epoxy resin may be spread over the copper wires and face of the transducer element at face of the carrier in order to present a smooth surface for insertion into the fuel assembly. The damping material 26 is composed of two grades of tungsten powder mixed in a low molecular weight polysulfide polymer. A specific damping material includes a mixture of a tungsten powder of an average particle size of 4.5 microns with a tungsten powder of an average particle size of 1.33 microns mixed with a low molecular weight polysulfide polymer called Thiokol LP-3, manufactured by the Thiokol Chemical Corporation, Trenton, New Jersey. A non-conducting epoxy resin is used to secure the transducer element within the aperture. The recessed surface of the ceramic is connected to the inner conductor of a coaxial cable which is disposed along the edge of the carrier. Other arrangements, shapes and materials can be used for the transducer element as long as the search unit is insertable between the components of the fuel assembly. In an alternate embodiment, for example, a hollow tubular carrier within which the coaxial cable is contained might be used.

Figure 3:
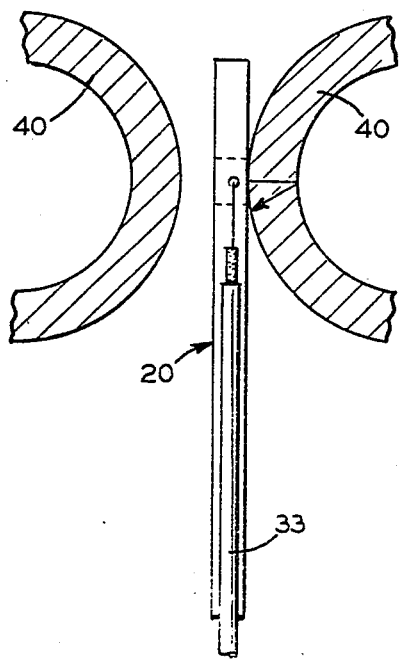
FIG. 3 is a schematic representation, using the apparatus embodied in FIG. 1, illustrating the echo of a radial pulse of ultrasound in a gas filled fuel element.
Figure 4:
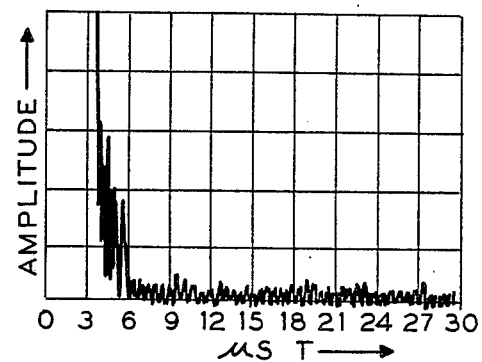
FIG. 4 is an oscillogram of the pulse and echo characterizing the response of the gas filled fuel element of FIG. 3.
Figure 6:
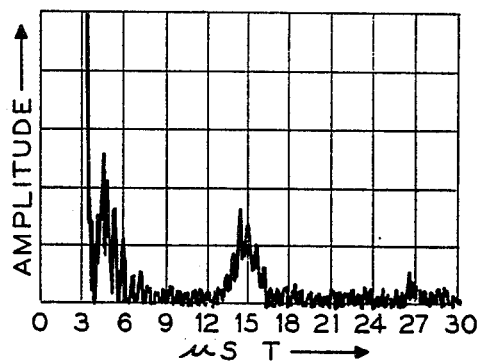
FIG. 6 is an oscillogram of the pulse and echo characterizing the response of the water filled fuel element of FIG. 5.
Figure 7:
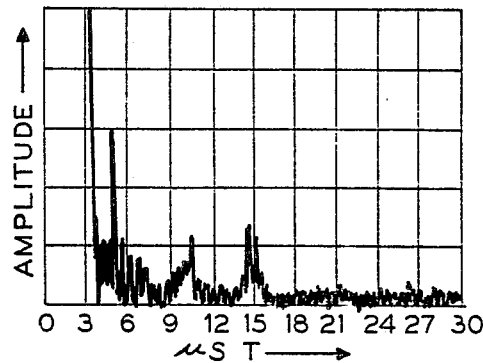
FIG. 7 is an oscillogram of the pulse and echo characterizing the response of a water-filled fuel element having a lower plenum spring.

FIG. 3 shows, as a section of a fuel assembly, a schematic planar representation of a search probe 20 transversely aligned with the lower plenum of a fuel element 40. The transducer element, coupled to the fuel element 40 for transmitting ultrasonic energy into the fuel element, is energized by a pulser (not shown) to emit pulses at a predetermined rate and frequency. The sweep of an oscilloscope is synchronized to display the transmitted and reflected pulses. The reflected waves are received by the scope via the transducer. If the fuel element has not failed, then gas will be the only fluid present in the lower plenum. A high reflection coefficient at the metal-gas interface will prevent significant propagation of the ultrasound past the inner surface of the cladding. The response displayed on a conventional pulse echo instrument for a gas filled fuel element is shown as an oscillogram in FIG. 4 with time (t) plotted as the abscissa. The oscillogram of FIG. 4, and also FIGS. 6 and 7, is representative of the resulting display generated at a frequency of approximately seven megahertz wherein each division of the time scale is approximately three microseconds and the fuel element outside diameter is slightly below 0.5 inches. In FIG. 4, the transmitted signal is substantially mixed with the received signal reflected from the first or front gas-metal interface due to the low coefficient of transmission of the gas.

Figure 5:
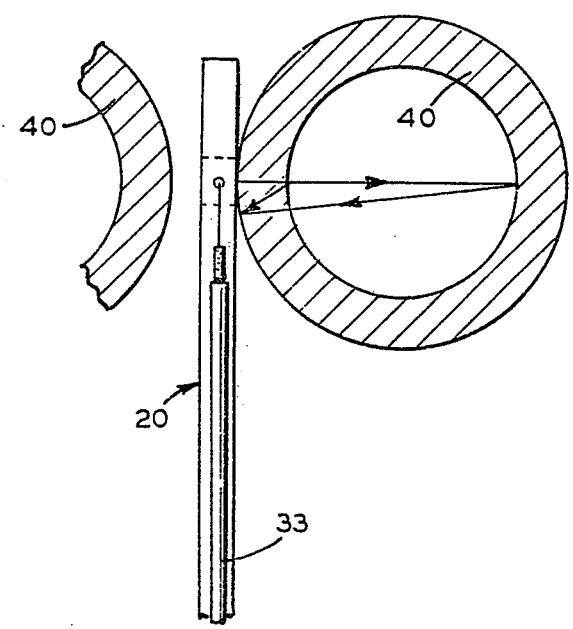
FIG. 5 is a schematic representation, using the apparatus embodied in FIG. 1, illustrating the echo of a radial pulse of ultrasound in a defective water filled fuel element.

If, in contrast, the fuel element has failed so that the lower plenum contains water, the reflection coefficient at the front interface will be significantly diminished. Thus, as schematically shown in FIG. 5, significant portions of the ultrasonic pulse will propagate through the liquid and be reflected at the back liquid-metal interface within the fuel element 40. Hence, a reflected signal of a relatively pronounced magnitude separated from the transmitted signal on the time scale will be displayed. The response displayed on a coventional pulse echo instrument for a defective, water filled fuel element is shown as an oscillogram in FIG. 6. A significant response occurs at approximately fifteen microseconds on the abscissa—this represents the echo received from the back wall.

The lower plenum of a fuel element generally contains a helical spring member which may restrict the free passage of the ultrasound. This does not, however, present an insurmountable difficulty. If the width of the piezoelectric element, measured along the longitudinal axis of the fuel element is greater than the pitch of the helical spring, then sound will propagate to the far wall and return. FIG. 7 shows the typical response of a water filled element containing a spring.

Conventional ultrasound instruments contain gating circuits that allow the extraction of signals during a selected period of time relative to an initial pulse. In addition, circuitry can be provided to produce an alarm signal only when the ultrasonic signal amplitude in the gated period exceeds a preset threshold level. If the gate is set to pass signals between twelve and fifteen microseconds on the abscissa, and if the amplitude threshold is set at line 1 of the ordinate, then the presence of water is detectable in a fuel element with or without springs.

In operation, the search unit is inserted into the spacing between adjacent components of the fuel assembly. Irradiated fuel assemblies are generally maintained under water, for cooling and shielding purposes, during removal from a reactor and initially are stored in a spent fuel pool. Hence, it will be understood that the inspection of the fuel elements is effected under water. The transducer element is transversely aligned with the longitudinal axis of the fuel element to be examined. A pulse is then emitted from the transducer into the fuel element.

A fuel assembly can be tested by insertion of the search unit into the bundle of fuel elements without any component disassembly. Hence, the assembly need only be removed from the reactor for inspection purposes.

The technique can be expanded to use multiplexed transducers to examine all the fuel elements of a fuel assembly automatically and rapidly.

I claim:

1. An ultrasonic search unit for testing nuclear fuel elements to detect the presence of water in fuel elements spaced within a fuel assembly of the type used in a water cooled nuclear reactor comprising a strip carrier with mutually opposing faces, the strip carrier being dimensioned to freely traverse the spaces between the fuel elements and having an integral aperture, an ultrasonic transducer element, electrodes deposited on at least two sides of the transducer element, the ultrasonic transducer element disposed within the aperture with one of the electrodes being flush with one of the strip carrier faces, means for grounding the ultrasonic transducer element to the strip carrier, means for decoupling said ultrasonic transducer element from the strip carrier, said decoupling means being interposed between the ultrasonic transducer element and the surfaces of the strip carrier defining the aperture, damping means disposed within the aperture adjacent to a recessed portion of the ultrasonic transducer element, and means for energizing the ultrasonic transducer element to transmit an ultrasonic pulse transversely into the wall of the fuel element to be tested.

2. An ultrasonic search unit as defined by claim 1, wherein the ultrasonic transducer element is a ferroelectric ceramic.

3. An ultrasonic search unit as defined by claim 2, wherein the ferroelectric ceramic is lead titanate zirconate.

4. An improved apparatus, for the in situ testing of a nuclear fuel element within a fuel assembly having a plurality of fuel elements closely packed in an array, transversely spaced within the array by spaces on the order of two millimeters, of the type in which an ultrasonic transducer element emits ultrasonic energy into the fuel element under water to detect the presence of water within the fuel element, wherein the improvement comprises: a strip carrier dimensioned to freely traverse the spaces between the fuel elements, the strip carrier having portions defining an integral aperture; the ultrasonic transducer element disposed within the aperture flush with one face of the strip carrier; means for decoupling the ultrasonic transducer element from the strip carrier, said decoupling means being interposed between the ultrasonic transducer element and the surfaces of the strip carrier defining the aperture; damping means disposed within the aperture adjacent to a recessed portion of the ultrasonic transducer element; and means operatively attached to the ultrasonic transducer element for energizing the ultrasonic transducer element to transmit an ultrasonic pulse transversely into the wall of a fuel element to be tested within the fuel assembly.

5. The improved apparatus, as set forth in claim 4, further comprising means for measuring a signal corresponding to the ultrasonic echo reflected from the inner wall surface of the fuel element remote from the location of the transducer element and for differentiating between echos transmitted through gas and water.

6. An apparatus for the in situ testing of a nuclear fuel element in a fuel assembly of the type used in a water cooled nuclear reactor wherein a plurality of fuel elements are separated by spaces on the order of two millimeters, comprising in combination: an ultrasonic transducer element; a strip carrier, having an aperture, dimensioned to freely traverse the spaces between the fuel elements; the transducer element being secured within the aperture flush with a face of the strip carrier; means mounted on the strip carrier and operatively attached to the transducer element for conducting a signal for energizing the transducer element to transmit an ultrasonic pulse transversely into the wall of the fuel element to be examined at a predetermined rate and frequency; means for measuring a signal corresponding to the ultrasonic echos reflected from the inner wall surface of the fuel element remote from the location of the transducer element; and means for differentiating between echos reflected through gas and water within the fuel element.

7. An apparatus as set forth in claim 6 further comprising an ultrasonic decoupling material disposed between the surfaces of the aperture and the ultrasonic transducer element.

8. An apparatus as set forth in claim 7 wherein the decoupling material is cork.

9. An apparatus as set forth in claim 8 wherein the ultrasonic transducer element is a ferroelectric ceramic.

10. An apparatus as set forth in claim 9 wherein the ferroelectric ceramic is lead titanate zirconate.

11. An apparatus as set forth in claim 10 wherein the ultrasonic transducer element measures approximately 2.5 millimeters wide, 12.5 millimeters long and 0.3 millimeters thick.

12. An apparatus as set forth in claim 7 further comprising a sonic damping material, said sonic damping material being disposed in the aperture adjacent the face of the transducer element recessed within the aperture.

13. An apparatus as set forth in claim 12 wherein the damping material consists essentially of tungsten powder mixed in a low molecular weight polysulfide polymer.

14. An apparatus as set forth in claim 6 further comprising means for energizing the ultrasonic transducer element to transmit ultrasonic waves in a frequency range of 5 to 15 megahertz.

* * * * *